(12) United States Patent
Law (10) Patent No.: US 7,256,308 B2
(45) Date of Patent: Aug. 14, 2007

(54) PROCESS FOR THE PRODUCTION OF ACETIC ACID

(75) Inventor: David John Law, Beverley (GB)

(73) Assignee: BP Chemicals Limited, Middlesex (GB)

( * ) Notice: Subject to any disclaimer, the term of this patent is extended or adjusted under 35 U.S.C. 154(b) by 256 days.

(21) Appl. No.: 10/514,148

(22) PCT Filed: May 29, 2003

(86) PCT No.: PCT/GB03/02352

§ 371 (c)(1),
(2), (4) Date: Nov. 12, 2004

(87) PCT Pub. No.: WO03/104179

PCT Pub. Date: Dec. 18, 2003

(65) Prior Publication Data

US 2005/0131251 A1 Jun. 16, 2005

(30) Foreign Application Priority Data

Jun. 6, 2002 (GB) ................................. 0212974.0

(51) Int. Cl.
*C07C 51/12* (2006.01)
(52) U.S. Cl. ...................................................... 562/519
(58) Field of Classification Search .................... None
See application file for complete search history.

(56) References Cited

FOREIGN PATENT DOCUMENTS

| EP | 1 099 680 A | 5/2001 |
|---|---|---|
| EP | 1 099 681 A | 5/2001 |

*Primary Examiner*—Paul A. Zucker
(74) *Attorney, Agent, or Firm*—Nixon & Vanderhye (57) ABSTRACT

A process for the production of acetic acid by carbonylating methanol and/or a reactive derivative thereof in a carbonylation reactor in a liquid reaction composition comprising an iridium carbonylation catalyst, methyl iodide, methyl acetate, water, acetic acid and at least one promoter selected from the group consisting of ruthenium, rhenium and osmium, characterized in that there is also present in the reaction composition a bis-phosphonate compound having the formula (I): wherein $R^1$, $R^2$, $R^3$, $R^4$ are independently hydrogen or an organic functional group; Y is an optionally substituted $C_1$-$C_{10}$ alkylene or $C_6$-$C_{10}$ aryl group.

19 Claims, 2 Drawing Sheets

PROCESS FOR THE PRODUCTION OF ACETIC ACID

This application is the U.S. National Phase of International Application PCT/GB03/02352, filed 29 May 2003, which designated the U.S. PCT/GB03/02352 claims priority to British Application No. 0212974.0 filed 6 Jun. 2002. The entire content of these applications are incorporated herein by reference.

The present invention relates to a process for the production of acetic acid by the carbonylation of methanol and in particular to a process for the production of acetic acid by the carbonylation of methanol in the presence of an iridium carbonylation catalyst and a promoter.

The production of acetic acid by the carbonylation of methanol in the presence of an iridium catalyst and ruthenium promoter is described for example in U.S. Pat. No. 5,672,743, EP-A-0752406, EP-A-0849248, EP-A-0849249, EP-A-0849250, EP-A-0999198 and EP-A-1002785. In such liquid phase carbonylation processes, the acetic acid product may be recovered by withdrawing the liquid carbonylation composition from the carbonylation reactor subjecting the composition to one or more separation stages to recover the acetic acid product and returning other components of the composition to the carbonylation reactor.

EP-A-0728729 relates to a process for purifying a carboxylic acid fraction obtained by liquid phase carbonylation in which volatile iridium and/or volatile co-promoter (such as ruthenium, osmium and rhenium) contaminants are converted to involatile forms by contacting with an iodide in the absence or carbon monoxide or at a partial pressure of carbon monoxide less than that of the carbonylation reaction. It is stated therein that the partial pressure of carbon monoxide may be from 0 to 5 bar, preferably less than 0.25 bar. The addition of phosphonate compounds to the liquid reaction composition is not considered.

The use of polydentate phosphine oxide compounds is known from EP-A-1099681, which relates to a process for the production of acetic acid by carbonylation of methanol and/or reactive derivative thereof in the presence of an iridium catalyst and a polydenate phosphine oxide compound in an amount of less than 10 mol per gram atom iridium.

There remains a need for an alternative and/or improved carbonylation process in which the partial pressure of the carbon monoxide during the acetic acid recovery stage and optional further reaction zone(s) may be reduced. A reduction in the partial pressure of carbon monoxide during product recovery allows an increase in the carbon efficiency of the carbonylation process.

It has now been found that by using certain bis-phosphonate compounds in an iridium-catalysed carbonylation process for the production of acetic acid, the partial pressure of carbon monoxide during the acetic acid recovery stage may be decreased.

In addition, the use of certain bis-phosphonate compounds in an iridium-catalysed carbonylation process for the production of acetic acid, allows high concentrations of promoter to be used resulting in the reduced formation of hydrogen and/or carbon dioxide by-products and an increased reaction rate.

Thus, according to the present invention, there is provided a process for the production of acetic acid by carbonylating methanol and/or a reactive derivative thereof in a carbonylation reactor in a liquid reaction composition comprising an iridium carbonylation catalyst, methyl iodide, methyl acetate, water, acetic acid and at least one promoter selected from the group consisting of ruthenium, rhenium and osmium, characterised in that there is also present in the reaction composition a bis-phosphonate compound having the formula:

wherein $R^1$, $R^2$, $R^3$, $R^4$ are independently hydrogen or an organic functional group; Y is an optionally substituted $C_1$-$C_{10}$ alkylene or $C_6$-$C_{10}$ aryl group.

The present invention also provides a process for the production of acetic acid which process comprises the steps of (1) carbonylating methanol and/or a reactive derivative thereof in a carbonylation reactor in a liquid reaction composition comprising iridium carbonylation catalyst, methyl iodide, methyl acetate, acetic acid, water, at least one promoter selected from the group consisting of ruthenium, rhenium and osmium and a bis-phosphonate compound having the formula:

wherein $R^1$, $R^2$, $R^3$, $R^4$ are independently hydrogen or an organic functional group; Y is an optionally substituted $C_1$-$C_{10}$ alkylene or $C_6$-$C_{10}$ aryl group;

(2) withdrawing liquid reaction composition together with dissolved and/or entrained carbon monoxide and other gases from said carbonylation reactor;

(3) optionally passing said withdrawn liquid reaction composition through one or more further reaction zones to consume at least a portion of the dissolved and/or entrained carbon monoxide;

(4) passing said composition from step (2) and optional step (3) into one or more flash separation stages to form (i) a vapour fraction comprising condensable components and low pressure off-gas, the condensable components comprising acetic acid product and the low pressure off-gas comprising carbon monoxide and other gases dissolved and/or entrained with the withdrawn liquid carbonylation reaction composition and (ii) a liquid fraction comprising iridium carbonylation catalyst, promoter and acetic acid solvent;

(5) separating the condensable components from the low pressure off-gas; and (6) recycling the liquid fraction from the flash separation stage to the carbonylation reactor.

Advantageously, the use of the bis-phosphonate compounds of the present invention in a process for the production of acetic acid allows a reduction in the amount of propanoic acid by-product produced even at low partial pressures of carbon monoxide.

In addition the use of certain bis-phosphonate compounds in an iridium-catalysed carbonylation process for the production of acetic acid provides improved catalyst system (catalyst and promoter) stability at low carbon monoxide partial pressure during product recovery.

Thus, the present invention also provides for the use of a bis-phosphonate compound of formula:

wherein $R^1$, $R^2$, $R^3$, $R^4$ are independently hydrogen or an organic functional group; Y is an optionally substituted $C_1$-$C_{10}$ alkylene or $C_6$-$C_{10}$ aryl group, in a process for the production of acetic acid to reduce the amount of by-product propanoic acid and/or to stabilise the catalyst system, said process comprising the steps of:

(a) carbonylating methanol and/or a reactive derivative thereof in a carbonylation reactor in a liquid reaction composition comprising an iridium carbonylation catalyst, methyl iodide, methyl acetate, water, acetic acid and at least one promoter selected from the group consisting of ruthenium, rhenium and osmium, withdrawing liquid reaction composition together with dissolved and/or entrained carbon monoxide and other gases from said carbonylation reactor;

(b) optionally passing said withdrawn liquid reaction composition through one or more further reaction zones to consume at least a portion of the dissolved and/or entrained carbon monoxide;

(c) passing said composition from step (a) and optional step (b) into one or more flash separation stages to form (i) a vapour fraction comprising condensable components and low pressure off-gas, the condensable components comprising acetic acid product and the low pressure off-gas comprising carbon monoxide and other gases dissolved and/or entrained with the withdrawn liquid carbonylation reaction composition and (ii) a liquid fraction comprising iridium carbonylation catalyst, promoter and acetic acid solvent;

(d) separating the condensable components from the low pressure off-gas;

(e) recycling the liquid fraction from the flash separation stage to the carbonylation The organic functional group ($R^1$, $R^2$, $R^3$ or, $R^4$) is suitably an unsubstituted or substituted hydrocarbon group, such as an unsubstituted or substituted alkyl, aryl, or cycloalkyl group.

Suitably, the hydrocarbon group is an alkyl group such as $C_1$ to $C_{15}$ alkyl or an aryl group such as $C_6$ to $C_{10}$ aryl.

The hydrocarbon group may be substituted by one or more substituents.

Suitably the substituted hydrocarbon group may be a $C_1$ to $C_{10}$ alkyl or a $C_6$ to $C_{10}$ aryl group substituted by one or more of —$NH_2$, —$NO_2$, —SH, halogen, —$CO_2R^5$, —$COR^6$, —$OR^7$, —COX, —$CSX^1$, —CN, —NCS or —NCO wherein $R^5$, $R^6$ and $R^7$ are independently hydrogen, an unsubstituted or substituted hydrocarbon group such as a $C_1$-$C_{10}$ alkyl or a $C_6$ to $C_{10}$ aryl, optionally substituted with one or more heteroatoms such as oxygen, nitrogen or sulphur; X and $X^1$ are independently selected from —$NH_2$, —$NO_2$, —SH, hydrogen, —$CH_3$, —$(CH_2)n$ $X^2$, halogen, —$CO_2R^8$, —$COR^9$, —$COX^3$, —$CSX^4$, —CN, —NCS or —NCO wherein $R^8$ and $R^9$ are as defined for $R^5$ or $R^6$ or $R^7$ and $X^2$, $X^3$ and $X^4$ are defined as for X or $X^1$; n is 1-10.

Suitably, the substituted hydrocarbon group may be —$(CH^2)nX^5$ where n is 1-10, —$CHX^6X^7$, $CX^8X^9X^{10}$ where $X^5$, $X^6$, $X^7$, $X^8$, $X^9$ and $X^{10}$ are as defined for X or $X^1$.

The organic functional group may comprise nitrogen, oxygen, sulphur atoms or mixtures thereof. Suitably the organic functional group may be —$CO_2R^{10}$, —$SO_2R^{11}$, —$COR^{12}$, —$COX^{11}$, —$CSX^{12}$, —CN, —NCS or —NCO where $R^{10}$, $R^{11}$, $R^{12}$, are as defined for $R^5$ or $R^6$ or $R^7$; $X^{11}$ and $X^{12}$ are as defined for X or $X^1$.

Suitably, where the organic functional group is an aryl group, such as $C_6$-$C_{10}$ aryl, it may be substituted by one or more heteroatoms, such as sulphur, oxygen, nitrogen or combinations thereof.

Preferably, $R^1$-$R^4$ are each hydrogen, or are each a $C_1$-$C_{15}$ alkyl group such as —$CH_3$ or a —$CH(CH_3)_2$ group.

Y is an optionally substituted $C_1$-$C_{10}$ alkylene group such as a $C_3$-$C_{10}$ cycloalkyl group or Y is an optionally substituted $C_6$-$C_{10}$ aryl group. The (cyclo)alkyl or aryl group may be substituted by one or more substituents such as those defined for X or $X^1$ above.

Y is preferably an unsubstituted $C_1$-$C_{10}$ alkylene group such as —$CH_2$, —$(CH_2)_2$—, $C_3$-$C_{10}$ cycloalkyl or a substituted $C_6$-$C_{10}$ aryl, such as a substituted benzene. Most preferably Y is a 1,2 disubstituted benzene or a $C_3$-$C_{10}$ cycloalkyl group.

Suitably, $R^1$-$R^4$ are each hydrogen, or are each a $C_1$-$C_{15}$ alkyl group such as —$CH_3$ or a —$CH(CH_3)_2$ group and Y is an unsubstituted $C_1$-$C_{10}$ alkylene group such as —$CH_2$, —$CH_2)_2$—, or an optionally substituted $C_3$—$C_{10}$ cycloalkyl group or an optionally substituted $C_6$-$C_{10}$ aryl such as a substituted benzene, for example, a 1,2 disubstituted benzene ring.

Suitable bis-phosphonate compounds are tetraisopropyl 1,2 ethylene diphosphonate, methylene diphosphonic acid and bis 1,2 dimethoxyphosphoryl benzene.

The bis-phosphonate compound may be present in the reaction composition in an amount such that catalyst activity is maintained as the amount of carbon monoxide in the low-pressure off-gas is reduced.

Suitably, the molar ratio of bis-phosphonate compound: iridium is in the range [0.1 to 10]:1, preferably, [0.5 to 5]:1, such as [0.5 to 2]:1 and especially [1 to 2]:1.

The bis-phosphonate compounds employed in the present invention may be added as such to the liquid reaction composition or may be formed in-situ, for example by the addition of the conjugate bis-phosphinic acid.

The first reaction zone may comprise a conventional liquid-phase carbonylation reaction zone. The pressure of the carbonylation reaction in the first reaction zone is suitably in the range 15 to 200 barg, preferably 15 to 100 barg, more preferably 15 to 50 barg and yet more preferably 18 to 35 barg. The temperature of the carbonylation reaction in the first reaction zone is suitably in the range 100 to 300° C., preferably in the range 150 to 220° C.

Preferably, two reaction zones are used. The reaction zones may be in the same or separate vessels. Preferably, the first and second reaction zones are maintained in separate reaction vessels with means for withdrawing from the first reaction vessel and passing to the second reaction vessel liquid reaction composition from the first reaction vessel with dissolved and/or entrained carbon monoxide. Such a separate second reaction vessel may comprise a section of pipe between the first reaction vessel and a liquid reaction composition flashing valve. Typically the pipe's length to diameter ratio may be about 12:1, though length to diameter ratios both higher and lower than this may be employed.

Typically, at least a portion of the liquid reaction composition together with dissolved and/or entrained carbon monoxide is withdrawn from the first reaction zone and at least a portion of the withdrawn liquid and dissolved and/or entrained carbon monoxide passed to a second reaction zone. Preferably substantially all the liquid reaction composition together with dissolved and/or entrained carbon monoxide withdrawn from the first reaction zone is passed to the second reaction zone.

The second reaction zone may be operated at a reaction temperature in the range 100 to 300° C., preferably in the range 150 to 230° C. The second reaction zone may be operated at a temperature higher than the first reaction zone, typically up to 30° C. higher. The second reaction zone may be operated at a reaction pressure in the range 10 to 200 barg, preferably in the range 15 to 100 barg. Preferably, the reaction pressure in the second reaction zone is equal to or less than the reaction pressure in the first reaction zone. The residence time of liquid reaction composition in the second reaction zone is suitably in the range 5 to 300 seconds, preferably 10 to 100 seconds.

There may be introduced to the second reaction zone carbon monoxide in addition to that introduced to the second reaction zone as dissolved and/or entrained carbon monoxide. Such additional carbon monoxide may be co-joined with the first liquid reaction composition prior to introduction to the second reaction zone and/or may be fed separately to one or more locations within the second reaction zone. Such additional carbon monoxide may contain impurities, such as for example $H_2$, $N_2$, $CO_2$ and $CH_4$. The additional carbon monoxide may be comprised of high pressure off-gas from the first reaction zone which could advantageously allow the first reaction zone to be operated at a higher CO pressure with the resulting higher flow of carbon monoxide being fed to the second reaction zone. Additionally it could eliminate the requirement for a high pressure off-gas treatment.

The additional carbon monoxide may also be comprised of another carbon monoxide-containing gas stream such as for example a carbon monoxide-rich stream from another plant.

Preferably greater than 10%, more preferably greater than 25%, even more preferably greater than 50%, such as 85%, for example at least 95%, of the dissolved and/or entrained carbon monoxide in the withdrawn reaction composition from the first reaction zone is consumed in the second reaction zone.

In the process of the present invention, suitable reactive derivatives of methanol include methyl acetate, dimethyl ether and methyl iodide. A mixture of methanol and reactive derivatives thereof may be used as reactants in the process of the present invention. Water is required as co-reactant for ether or ester reactants. Preferably, methanol and/or methyl acetate are used as reactants.

At least some of the methanol and/or reactive derivative thereof will be converted to, and hence present as, methyl acetate in the liquid reaction composition by reaction with the carboxylic acid product or solvent. Preferably, the concentrations of methyl acetate in the liquid reaction compositions in the first and second reaction zones are independently in the range 1 to 70% by weight, more preferably 2 to 50% by weight, most preferably 3 to 35% by weight.

Water may be formed in situ in the liquid reaction compositions, for example, by the esterification reaction between methanol reactant and acetic acid product. Water may be introduced independently to the first and second carbonylation reaction zones together with or separately from other components of the liquid reaction compositions. Water may be separated from other components of reaction compositions withdrawn from the reaction zones and may be recycled in controlled amounts to maintain the required concentration of water in the liquid reaction compositions. Preferably, the concentrations of water in the liquid reaction compositions in the first and second reaction zones are independently in the range 0.1 to 20% by weight, more preferably 1 to 15% by weight, yet more preferably 1 to 10% by weight.

Preferably, the concentration of methyl iodide co-catalyst in the liquid carbonylation reaction compositions in the first and second reaction zones is independently in the range 1 to 20% by weight, preferably 2 to 16% by weight.

The iridium catalyst in the liquid reaction compositions in the first and second reaction zones may comprise any iridium-containing compound which is soluble in the liquid reaction compositions. The iridium catalyst may be added to the liquid reaction compositions in any suitable form which dissolves in the liquid reaction compositions or is convertible to a soluble form. Preferably the iridium may be used as a chloride free compound such as acetates which are soluble in one or more of the liquid reaction composition components, for example water and/or acetic acid and so may be added to the reaction as solutions therein. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H^+$, $[Ir(CH_3)I_3(CO)_2]^-H^+$, $Ir_4(CO)_{12}$, $IrCl_3.4H_2O$, $IrBr_3.4H_2O$, $Ir_3(CO)_{12}$, iridium metal, $Ir_2O_3$, $IrO_2$, $Ir(acac)(CO)_2$, $Ir(acac)_3$, iridium acetate, $[Ir_3O(OAc)_6(H_2O)_3][OAc]$, and hexachloroiridic acid $H_2[IrCl_6]$, preferably, chloride-free complexes of iridium such as acetates, oxalates and acetoacetates.

Preferably, the concentration of the iridium catalyst in the liquid reaction compositions of the first and second reaction zones is independently in the range 100 to 6000 ppm by weight of iridium.

The liquid reaction compositions in the first and second reaction zones additionally comprises at least one promoter selected from the group consisting of ruthenium, rhenium and osmium. The promoter may comprise any ruthenium, rhenium and/or osmium-containing compound which is soluble in the liquid reaction compositions. The promoter may be added to the liquid reaction compositions in any suitable form which dissolves in the liquid reaction compositions or is convertible to soluble form. Preferably, the promoter compound may be used as chloride-free compounds such as acetates which are soluble in one or more of the liquid reaction composition components, for example water and/or acetic acid and so may be added to the reaction as solutions therein.

Examples of suitable ruthenium-containing compounds which may be used include ruthenium (III) chloride, ruthenium (III) chloride trihydrate, ruthenium (IV) chloride, ruthenium (III) bromide, ruthenium (III) iodide, ruthenium metal, ruthenium oxides, ruthenium (III) formate, $[Ru(CO)_3I_3]^-H^+$, tetra(aceto)chlororuthenium(II, III), ruthenium (III) acetate, ruthenium (III) propionate, ruthenium (III) butyrate, ruthenium pentacarbonyl, trirutheniumdodecacarbonyl and mixed ruthenium halocarbonyls such as dichlorotricarbonylruthenium (II) dimer, dibromotricarbonylruthenium (II) dimer, and other organoruthenium complexes such as tetrachlorobis(4-cymene)diruthenium(II), tetrachlorobis(benzene)diruthenium(II), dichloro(cycloocta-1, 5-diene)ruthenium (II) polymer and tris(acetylacetonate) ruthenium (III).

Examples of suitable osmium-containing compounds which may be used include osmium (III) chloride hydrate and anhydrous osmium metal, osmium tetraoxide, triosmiumdodecacarbonyl and mixed osmium halocarbonyls such as tricarbonyldichloroosmium (II) dimmer and other organoosmium complexes.

Examples of suitable rhenium-containing compounds which may be used include $Re_2(CO)_{10}$, $Re(CO)_5Cl$, $Re(CO)_5Br$, $Re(CO)I$, $ReCl_3.xH_2O$, $ReCl_5.yH_2O$ and $[\{Re(CO)_4I\}_2]$ Preferably, the promoter-containing compounds are free of impurities which provide or generate in-situ ionic iodides which may inhibit the reaction, for example, alkali or alkaline earth metal or other metal salts.

Preferably, the promoter is present in an effective amount up to the limit of its solubility in the liquid reaction compositions and/or any liquid process streams recycled to the carbonylation reaction zones from the acetic acid recovery stage. The promoter is suitably present in the liquid reaction compositions at a molar ratio of each promoter: iridium in the range [0.1 to 100]:1, preferably [greater than 0.5]:1, more preferably [greater than 1]:1 and preferably [up to 10]:1 such as [3 to 10]:1, [4 to 8]:1 or [4 to 6]:1.

Suitably, where the molar ratio of promoter:iridium is in the range [3 to 10]:1, the molar ratio of bis-phosphonate: iridium is in the range [0.5 to 5]:1.

The concentration of promoter in the liquid reaction compositions in each of the first and second reaction zones is, independently, less than 8000 ppm. A suitable promoter concentration is 400 to 7000 ppm, such as 2000 to 5000 ppm.

Although in general it is preferred to operate the process in the substantial absence of added iodide salt, i.e. a salt generating or dissociating an iodide ion, it may be possible under certain conditions to tolerate such a salt. Accordingly, ionic contaminants such as, for example, (a) corrosion metals, particularly nickel, iron and chromium and (b) phosphines or nitrogen-containing compounds or ligands which may quatemise in situ, should be kept to a minimum or eliminated in the liquid reaction composition as these may generally have an adverse effect on the reaction by generating $I^-$ in the liquid reaction composition which has an adverse effect on the reaction rate. Some corrosion metal contaminants such as for example molybdenum have been found to be less susceptible to the generation of $I^-$. Corrosion metals which have an adverse effect on the reaction rate may be minimised by using suitable corrosion resistant materials of construction. Similarly, contaminants such as alkali metal iodides, for example lithium iodide, should be kept to a minimum. Corrosion metal and other ionic impurities may be reduced by the use of a suitable ion exchange resin bed to treat the reaction composition, or preferably a catalyst recycle stream. Such a process is described in U.S. Pat. No. 4,007,130. Preferably, ionic contaminants are kept below a concentration at which they would generate less than 500 ppm $I^-$, preferably less than 250 ppm $I^-$ in the liquid reaction composition, more preferably less than 50 ppm $I^-$.

The carbon monoxide reactant for the carbonylation reactions may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in situ by the water gas shift reaction is preferably kept low, for example, less than 1 bar partial pressure, as its presence may result in the formation of hydrogenation products. The partial pressure of carbon monoxide in the first and second reaction zones is suitably independently in the range 1 to 70 bar, preferably 1 to 35 bar and more preferably 1 to 15 bar.

Acetic acid product may be recovered from the second reaction zone and optionally together with or separately from the first reaction zone by flash separation. In flash separation liquid reaction composition is passed to a flashing zone via a flashing valve. The flash separation zone may be an adiabatic flash vessel or may have additional heating means. In the flash separation zone a liquid fraction comprising the majority of the iridium catalyst and the majority of the promoter is separated from a vapour fraction comprising acetic acid, carbonylatable reactant, water and methyl iodide carbonylation co-catalyst and non-condensable gases such as nitrogen, carbon monoxide, hydrogen and carbon dioxide; the liquid fraction being recycled to the first reaction zone and the vapour fraction being passed to one or more distillation zones. In a first distillation zone acetic acid product is separated from the light components (methyl iodide and methyl acetate). The light components are removed overhead, and recycled to the first and/or second reaction zones. Also removed overhead is a low pressure off-gas comprising the non-condensable gases such as nitrogen, carbon monoxide, hydrogen and carbon dioxide. Such a low-pressure off-gas stream may be passed through an off-gas treatment section to remove condensable materials such as methyl iodide, prior to being vented to atmosphere, for example, via a flare.

Suitably, the concentration of carbon monoxide in the low pressure off gas is less than 40 mol %, preferably less than 20 mol % and the promoter concentration in the liquid reaction composition is up to 8000 ppm by weight.

The acetic acid produced by the process according to the present invention may be further purified by conventional processes, for example further distillation to remove impurities such as water, unreacted carbonylation reactant and/or ester derivative thereof and higher-boiling by-products.

The process of the present invention is preferably performed as a continuous process.

BRIEF DESCRIPTION OF THE DRAWINGS

The present invention will now be illustrated by way of example only and with reference to the following Examples and FIGS. 1 and 2.

GENERAL REACTION METHOD FOR EXPERIMENTS A AND B AND EXAMPLES 1-3

A 300 $cm^3$ zirconium autoclave, equipped with a stirrer and liquid injection facility was used for a series of batch autoclave experiments. The autoclave was pressure tested to $4 \times 10^6$ $N/m^2$ with nitrogen, then flushed three times with carbon monoxide up to $1 \times 10^6 N/m^2$. An initial charge consisting of methyl acetate (approx 48.0 g) acetic acid (approx 38.0 g) methyl iodide (approx 13.3 g) and water (approx 12.5 g) was placed into the autoclave, which was then repurged with carbon monoxide and vented slowly to prevent loss of volatiles. Carbon monoxide (approx $6-7 \times 10^5$ $N/m^2$) was placed in the autoclave, which was then heated, with stirring (1500 rpm) to 190° C. A catalyst injection system was primed with approx 5.6 g of iridium acetate catalyst solution (5.25% Ir w/w) and acetic acid (approx 8.7 g) and injected with an overpressure of carbon monoxide to the hot autoclave, to bring the autoclave pressure to $2.8 \times 10^6$ $N/m^2$.

The reaction rate was monitored by drop in carbon monoxide pressure from a ballast vessel, typically pressured to $7 \times 10^6$ $N/m^2$. The autoclave temperature and pressure were maintained at a constant 190° C. and $2.8 \times 10^6$ $N/m^2$ throughout the reaction by pressure and coolant control valves. The reaction was terminated when the drop in ballast pressure became less than $1 \times 10^4$ N/m² per 5 minutes.

After cooling, a gas analysis sample was taken, and the autoclave vented. The liquid components were discharged, and analysed for liquid by-products by gas chromatography. Detected components are quantified by integration of the component peaks relative to an external standard and expressed as parts per million (ppm) by weight.

In the experiments, 'Total' propanoic acid was defined as the sum of propanoic acid and its precursors (ethyl acetate and ethyl iodide) converted to ppm propanoic acid detected in the quenched liquid products of the batch reaction expressed in ppm.

The rate of gas uptake at a certain point in a reaction run was used to calculate the carbonylation rate, as number of moles of reactant consumed per litre of cold degassed reactor composition per hour (mol/(l×h) at a particular reactor composition (total reactor composition based on a cold degassed volume)

The methyl acetate concentration was calculated during the course of the reaction from starting composition, assuming that one mole of methyl acetate was consumed for every mole of carbon monoxide that was consumed. No allowance was made for organic components in the autoclave headspace.

By monitoring the rate of carbonylation reaction and calculating the concentration of the reaction components during the experiment, it is possible to determine the rate of carbonylation reaction which would be expected if a carbonylation process were to be operated continuously whilst maintaining under steady state, a liquid reaction composition which is the same as the total reaction composition calculated at any particular point in the batch experiment.

In the experiments the term 'reaction composition' refers to the total composition of the components in the autoclave in the cold degassed state.

Experiment A

A baseline experiment was performed with the autoclave charged with methyl acetate (48.05 g) acetic acid (53.00 g) ruthenium acetate (6.94 g) water (13.5 g) methyl iodide (13.33 g). The catalyst solution consisted of an iridium solution (6.3 g) (5.25% Ir w/w) with acetic acid (8.70 g). The approximate molar ratio of iridium to ruthenium was 1:2

The rate of reaction, based on carbon monoxide uptake was measured to be 20.3 mol/l/h at a calculated reaction composition of 15% methyl acetate and steadily declined until virtually all the methyl acetate was consumed.

Conversion to acetic acid was 98.9% based on methyl acetate consumed. Analysis of propanoic acid precursors gave a total propanoic acid make of 460 ppm. Gaseous by-products in the cold-vented off-gas were $H_2$ 2.8 mmol; $CO_2$ 3.2 mmol; $CH_4$ 5.2 mmol This is not an example according to the present invention because no bis-phosphonate compound was added to the liquid reaction composition.

Experiment B

A baseline experiment was performed with the autoclave charged with methyl acetate (48.05 g) acetic acid (48.42 g) ruthenium acetate (12.28 g) water (13.86 g) methyl iodide (13.31 g). The catalyst solution consisted of an iridium solution (6.15 g) (5.25% Ir w/w) with acetic acid (8.71 g). The approximate molar ratio of iridium to ruthenium was 1:4

The rate of reaction, based on carbon monoxide uptake was measured to be 23.4 mol/(l×h) at a calculated reaction composition of 15% methyl acetate and steadily declined until virtually all the methyl acetate was consumed.

Conversion to acetic acid was 99.2% based on methyl acetate consumed. Analysis of propionic acid precursors gave a total propionic acid make of 460 ppm. Gaseous by-products in the cold-vented off-gas were not analysed.

The cooled reaction mixture showed a clearly observable amount of precipitate.

This is not an example according to the present invention because no bis-phosphonate compound was added to the liquid reaction composition.

EXAMPLE 1

Experiment A was repeated except that bis dimethoxyphosphoryl benzene (dmpb) was added to the base of the autoclave in a molar ratio to Ir of 1:1. This is an example of the use of a bis-phosphonate compound according to the present invention. No precipitate could be observed in the cooled reaction mixture demonstrating increased catalyst stability under cool, carbon monoxide free conditions.

EXAMPLE 2

Experiment B was repeated except that bis-dimethoxyphosphoryl benzene was added to the base of the autoclave in a molar ratio to Ir of 1:2. This is an example of the use of a bis-phosphonate compound according to the present invention. No precipitate could be observed in the cooled reaction mixture.

EXAMPLE 3

Experiment B was repeated except that the molar ratio of Ir to Ru was increased to 1:6 and bis-dimethoxyphosphoryl benzene was added to the base of the autoclave in a molar ratio to Ir of 1:2. This is an example of the use of bis-dimethoxyphosphoryl benzene according to the present invention. No precipitate was observed in the cooled reaction mixture.

The results of Experiments A and B and Examples 1-3 are summarized in Table 1 below.

TABLE 1

| Experiment/Example | % conv. MeOAc | Rate at 15% MeOAc mol/(l × h) | $H_2$ (% v/v) | $CO_2$ (% v/v) | Total propanoic acid/ppm |
| --- | --- | --- | --- | --- | --- |
| (A) Ir: 2Ru | 98.9 | 20.3 | 2.8 | 3.2 | 460 |
| (B) Ir: 4Ru | 99.2 | 23.4 | n/a | n/a | 460 |
| (1) Ir: 2Ru: dmpb | 98.5 | 20.4 | 2.7 | 2.8 | 420 |
| (2) Ir: 4Ru: 2dmpb | 99.1 | 23.3 | 3.0 | 3.0 | 390 |
| (3) Ir: 6Ru: 2dmpb | 99.2 | 27.0 | 2.9 | 3.4 | 440 | n/a—data not available.

The results in Table 1 demonstrate that the use of a bis-phosphonate compound according the present invention in an iridium-catalysed carbonylation process to produce acetic acid, allows reduction in the amount propanoic acid by-product without adversely affecting the reaction rate o amount of hydrogen or carbon dioxide by-products.

GENERAL REACTION METHOD FOR EXPERIMENTS C TO H AND EXAMPLES 4 TO 23

Figure 1:
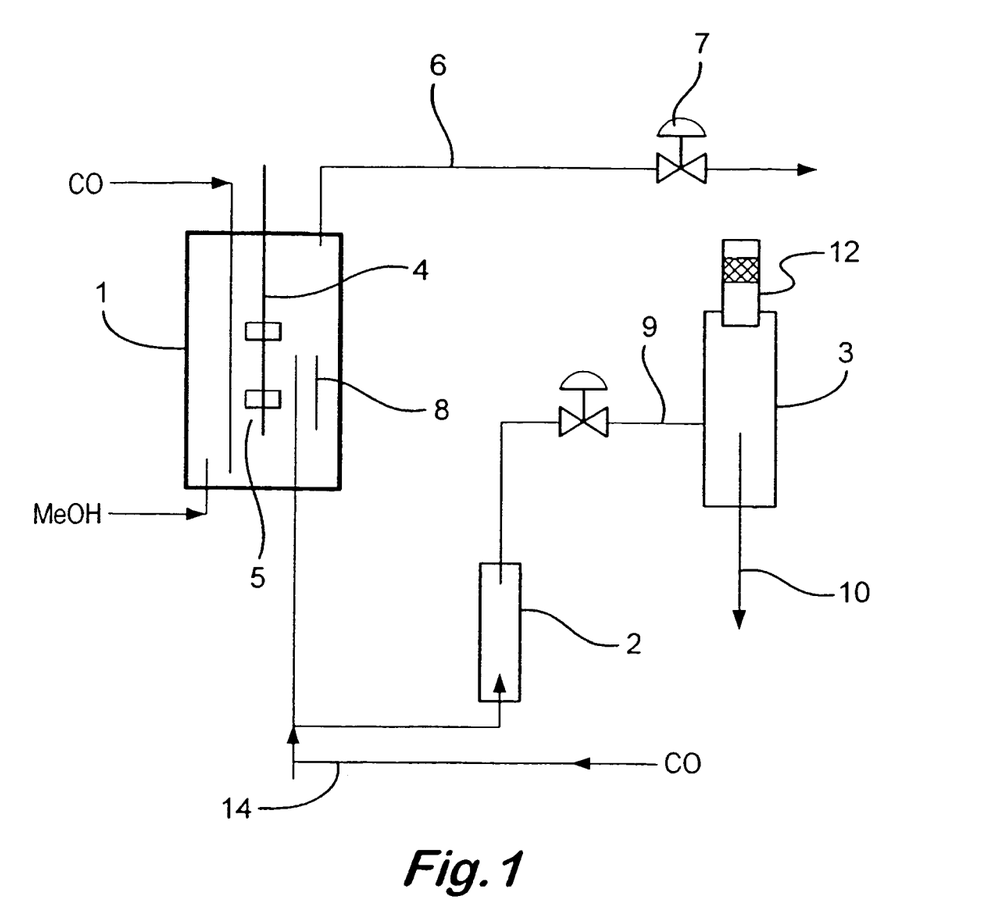
FIG. 1 is a schematic diagram of the apparatus used in the Examples.

The apparatus used is shown in FIG. 1. With reference to FIG. 1 the apparatus comprised a stirred primary carbonylation reactor (1), a secondary carbonylation reactor (2), a flash tank (3) and a distillation column (not shown).

Commercial grade methanol, which has been used to scrub the off-gas was carbonylated in the 6 litre primary reactor (1) in the presence of an iridium carbonylation catalyst and a ruthenium promoter at a pressure of $2.76 \times 10^6$ $N/m^2$ and a temperature of 190° C. The primary reactor (1) was fitted with a stirrer/propeller (4) and a baffle cage (not shown) to ensure intimate mixing of the liquid and gaseous reactants. Carbon monoxide was supplied to the primary reactor (1) via a sparge (5) fitted beneath the stirrer (4). To minimise iron ingress into the primary reactor (1) the carbon monoxide was passed through a carbon filter (not shown). A jacket (not shown), through which the hot oil is circulated, enabled the reaction liquid in the primary reactor (1) to be maintained at a constant reaction temperature. The liquid reaction composition was analysed by near infra-red analysis and gas chromatography To purge inerts, high pressure off-gas was removed from the primary reactor (1) through line (6). It was passed through a condenser (not shown) before the pressure was dropped across valve (7) and mixed with the low pressure off-gas for it to be fed into the scrubbing system. Liquid reaction composition was withdrawn from the primary reactor (1) down a still well (8), through the secondary reactor (2), and then via line (9) into the flash tank (3) under reactor level control. In the flash tank (3) the liquid reaction composition was flashed down to a pressure of $1.48 \times 10^5$ $N/m^2$. The resulting mixture of vapour and liquid was separated; the catalyst-rich liquid was returned to the primary reactor (1) by line (10) and pump (not shown) and the vapour was passed through a demister (12) and then directly into a distillation column (not shown) as vapour.

The secondary reactor (2) comprised a pipe of diameter 2.5 cm, length 30 cm and together with associated pipework had a volume of approximately 8% of the primary reactor (1). The pipe was placed in parallel to the flashing line (9), and was provided with a supply of additional carbon monoxide via line 14. The secondary reactor (2) was operated at approximately the same pressure as the primary reactor (1).

The vapour from the demister (12) enters the distillation column (not shown) where acetic acid is recovered from the vapour and a low pressure off-gas comprising carbon monoxide is passed to a scrubber (not shown) before being vented.

The degree of catalyst precipitation was measured in conjunction with the liquid reaction composition by near infra red spectroscopy. The increase in the baseline absorbance has been found to directly correlate with the amount of precipitation.

Experiment C

Using the apparatus and method as described with reference to FIG. 1, methanol was carbonylated in the primary reactor (1) at a rate of 20 mol/l/h (based on cold degassed reaction volume). The liquid reaction composition in the primary reactor (1) comprised approximately 7% by weight of methyl iodide, 12% by weight of methyl acetate, 5% by weight of water, approx. 76% by weight of acetic acid, 1400 ppm of iridium and 2940 ppm ruthenium. The liquid reaction composition was further carbonylated in the second reactor (2) at a mid temperature of 190° C. and a total pressure of approximately $27 \times 10^5$ $N/m^2$ with a residence time of 40-60 seconds.

Additional carbon monoxide was fed into the secondary reactor to maintain the concentration of carbon monoxide in the non-volatile components exiting the flash tank at 30 mol %. The results are shown in Table 2.

Experiments D to E

The process of Experiment C was repeated except the amount of carbon monoxide fed into the secondary carbonylation reactor was reduced in stages, until in Experiment E, there was no additional carbon monoxide fed into the secondary reactor. The results are shown in Table 2. No bis-phosphonate compound was added to the carbonylation reactor in Experiments D to E.

Experiments F to H

The processes of Examples C to E were repeated except the Ru:Ir ratio in the carbonylation reactor was increased to a molar ratio of 6:1. The results are shown in Table 2. No bis-phosphonate compound was added to the carbonylation reactor in Experiments F to H.

EXAMPLES 4 TO 23

The processes of Experiments C to H were repeated except various amounts of dmpb were added to the first carbonylation reactor. The results are shown in Table 2.

TABLE 2

| Experiment/ Example | Ir (ppm) | Ru:Ir (molar) | dmpb:Ir (molar) | [CO] in low pressure off gas (mol %) | Precipitation Rate | CO2 Rate (% carbn) | Propanoic acid/ ppm |
|---|---|---|---|---|---|---|---|
| C | 1290 | 4.1 | 0.0 | 30 | −0.001 | 0.9 | 510 |
| D | 1380 | 4.0 | 0.0 | 21 | 0.014 | 0.8 | 550 |
| E | 1270 | 4.0 | 0.0 | 11 | 0.190 | 0.8 | 560 |
| F | 1160 | 6.0 | 0.0 | 31 | 0.016 | 0.8 | 520 |
| G | 1180 | 6.0 | 0.0 | 20 | 0.141 | 0.8 | 540 |
| H | 1120 | 5.9 | 0.0 | 20 | 0.287 | 0.9 | 540 |
| 4 | 1390 | 4.1 | 0.3 | 31 | 0.002 | 1.0 | * |
| 5 | 1330 | 4.2 | 0.3 | 20 | 0.015 | 0.9 | * |
| 6 | 1230 | 6.0 | 0.5 | 20 | 0.132 | 0.9 | * |
| 7 | 1210 | 5.9 | 0.5 | 16 | 0.246 | 0.8 | * |

TABLE 2-continued

| Experiment/Example | Ir (ppm) | Ru:Ir (molar) | dmpb:Ir (molar) | [CO] in low pressure off gas (mol %) | Precipitation Rate | CO2 Rate (% carbn) | Propanoic acid/ppm |
|---|---|---|---|---|---|---|---|
| 8 | 1200 | 6.0 | 0.5 | 30 | 0.007 | 0.8 | * |
| 9 | 1190 | 6.0 | 1.0 | 30 | 0.007 | 0.9 | 460 |
| 10 | 1170 | 5.9 | 1.0 | 19 | 0.061 | 0.9 | 490 |
| 11 | 1220 | 5.6 | 0.9 | 17 | 0.074 | 0.8 | 490 |
| 12 | 1240 | 5.7 | 2.7 | 31 | 0.002 | 0.9 | 470 |
| 13 | 1190 | 6.2 | 2.8 | 23 | 0.036 | 0.8 | 500 |
| 14 | 1190 | 6.1 | 2.8 | 17 | 0.046 | 0.8 | 480 |
| 15 | 1560 | 4.0 | 1.9 | 29 | −0.005 | 0.9 | 510 |
| 16 | 1570 | 4.0 | 1.9 | 20 | −0.004 | 1.0 | 530 |
| 17 | 1525 | 4.1 | 1.9 | 12 | 0.036 | 1.0 | 540 |
| 18 | 1265 | 6.0 | 1.1 | 21 | 0.012 | 0.9 | 520 |
| 19 | 1210 | 5.7 | 1.1 | 17 | 0.039 | 0.9 | 500 |
| 20 | 1460 | 4.2 | 0.7 | 28 | 0.001 | 1.0 | 530 |
| 21 | 1500 | 4.2 | 0.7 | 20 | 0.004 | 1.0 | 540 |
| 22 | 1450 | 4.0 | 0.7 | 13 | 0.034 | 1.0 | 530 |
| 23 | 1510 | 4.1 | 0.3 | 12 | 0.045 | 1.1 | 560 |

* data not available

The results from Table 2 demonstrate that where dmpb has been added to the carbonylation reactor, the partial pressure of carbon monoxide in the low pressure off-gas can be decreased whilst maintaining catalyst stability and providing a reduction in the amount of propanoic acid by-product produced.

Figure 2:
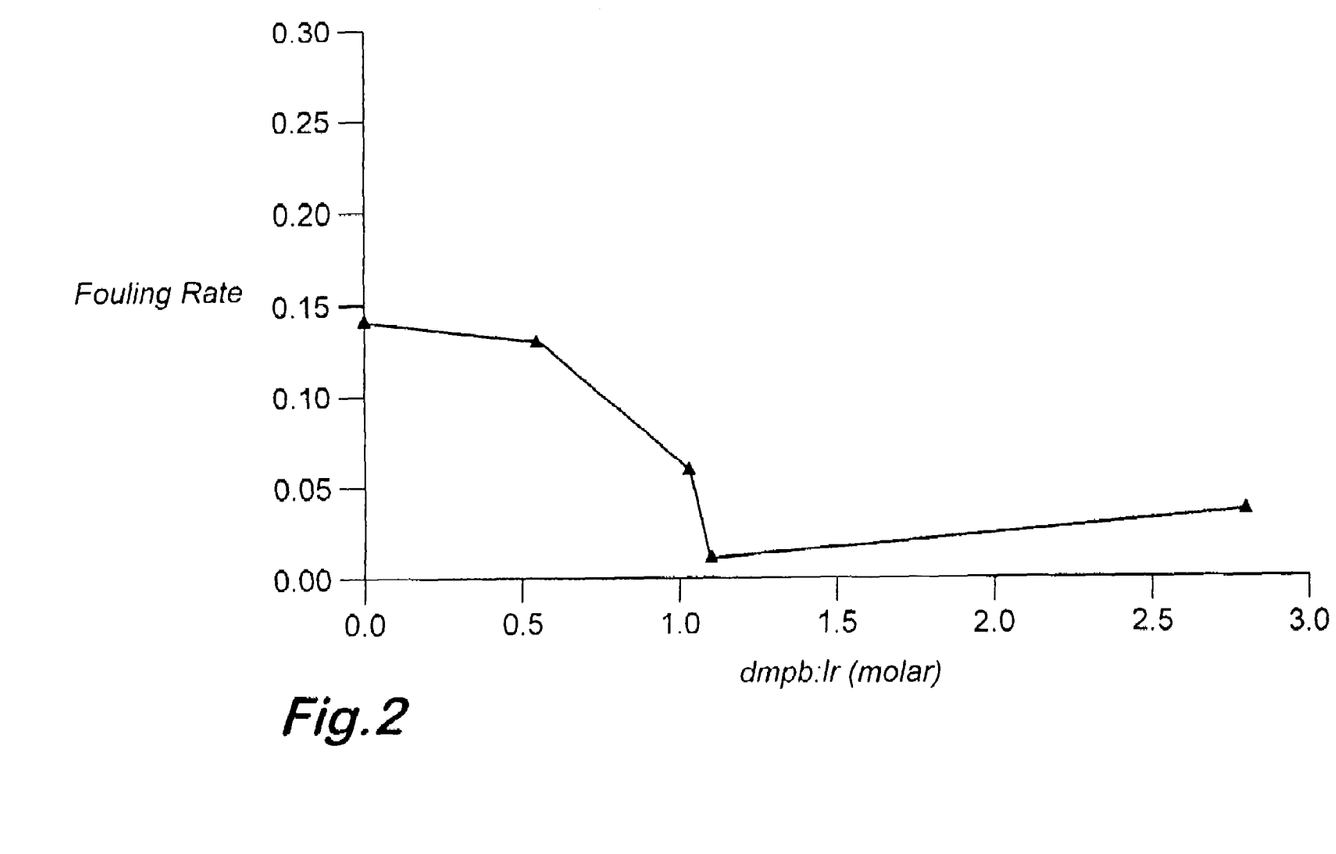
FIG. 2 is a graph of the effects of a bis-phosphonate compound on catalyst system stability for ca. 1200 ppm iridium with ca. 20% CO in the low-pressure off-gas.

FIG. 2 shows the beneficial effect of the addition of dmpb on catalyst stability at low carbon monoxide partial pressure in the low pressure off-gas from the flash tank At 20% carbon monoxide in the low pressure off-gas, catalyst stability is increased as the molar ratio of dmpb:Ir is increased. Each data point on the graph represents the rate of build-up of precipitate derived over 24 hours of experimentation.

The invention claimed is:

1. A process for the production of acetic acid, said process comprising carbonylating methanol and/or a reactive derivative thereof in a carbonylation reactor in a liquid reaction composition comprising an iridium carbonylation catalyst, methyl iodide, methyl acetate, water, acetic acid and at least one promoter selected from the group consisting of ruthenium, rhenium and osmium, wherein there is also present in the reaction composition a bis-phosphonate compound having the formula:

wherein $R^1$, $R^2$, $R^3$, $R^4$ are independently hydrogen or an organic functional group; Y is an optionally substituted $C_1$-$C_{10}$ alkylene or $C_6$-$C_{10}$ aryl group.

2. A process according to claim 1 wherein the process comprises the further steps of:
(a) withdrawing liquid reaction composition together with dissolved and/or entrained carbon monoxide and other gases from said carbonylation reactor;
(b) optionally passing said withdrawn liquid reaction composition through one or more further reaction zones to consume at least a portion of the dissolved and/or entrained carbon monoxide;
(c) passing said composition from step (a) and optional step (b) into one or more flash separation stages to form
(i) a vapour fraction comprising condensable components and low pressure off-gas, the condensable components comprising acetic acid product and the low pressure off-gas comprising carbon monoxide and other gases dissolved and/or entrained with the withdrawn liquid carbonylation reaction composition and
(ii) a liquid fraction comprising iridium carbonylation catalyst, promoter and acetic acid solvent;
(d) separating the condensable components from the low pressure off-gas; and
(e) recycling the liquid fraction from the flash separation stage to the carbonylation reactor.

3. A process according to claim 1 wherein $R^1$, $R^2$, $R^3$, $R^4$ are independently an organic functional group selected from the group consisting of an unsubstituted hydrocarbon group and a substituted hydrocarbon group.

4. A process according to claim 1 wherein $R^1$, $R^2$, $R^3$, $R^4$ are each hydrogen or are each an unsubstituted hydrocarbon group.

5. A process according to claim 4 wherein each unsubstituted hydrocarbon group is a —$CH_3$— group or a $CH(CH_3)_2$— group.

6. A process according to claim 1 wherein Y is selected from the group consisting of an unsubstituted $C_1$-$C_{10}$ alkylene group, an optionally substituted $C_6$-$C_{10}$ aryl and an optionally unsubstituted $C_3$-$C_{10}$ cycloalkyl.

7. A process according to claim 6 wherein the unsubstituted $C_1$-$C_6$ alkylene group is selected from the group consisting of —$CH_2$— and $(CH_2)_2$—.

8. A process according to claim 6 wherein the optionally substituted $C_6$-$C_{10}$ aryl is a substituted benzene.

9. A process according to claim 1 wherein Y is selected from the group consisting of an unsubstituted $C_1$-$C_{10}$ alkylene group, an optionally substituted $C_3$-$C_{10}$ cycloalkyl group and an optionally substituted $C_6$-$C_{10}$ aryl and $R^1$, $R^2$, $R^3$, $R^4$ are each hydrogen or are each an unsubstituted hydrocarbon group.

10. A process according to claim 8 wherein each unsubstituted hydrocarbon group is a methyl group.

11. A process according to claim 1 wherein the bis-phosphonate is selected from the group consisting of tetraisopropyl 1,2 ethylene diphosphonate, methylene diphosphonic acid and bis 1,2 dimethoxyphosphoryl benzene.

12. A process according to claim 1 wherein the bis-phosphonate is formed in-situ in the liquid reaction composition.

13. A process according to claim 1 wherein the bis-phosphonate compound is present in the liquid reaction composition at a molar ratio of bis-phosphonate compound:iridium in the range of [0.1 to 10]:1.

14. A process according to claim 13 wherein the molar ratio of bis-phosphonate compound:iridium is in the range [0.5 to 5]:1.

15. A process according to claim 13 wherein the molar ratio of bis-phosphonate compound:iridium is in the range [0.5 to 2]:1.

16. A process according to claim 1 wherein the promoter is present in the liquid reaction composition at a molar ratio of promoter:iridium in the range [up to 10]:1.

17. A process according to claim 16 wherein the molar ratio of promoter:iridium is in the range [3 to 10]:1.

18. A process according to claim 1 wherein the molar ratio of bis-phosphonate compound:iridium is in the range [0.5 to 5]:1 and the molar ratio of promoter:iridium is in the range [3 to 10]:1.

19. A process according to claim 2 wherein the concentration of carbon monoxide in the low pressure off-gas is less than 40 mol % and the concentration of promoter is up to 8000 ppm by weight.

* * * * *